United States Patent [19]

Engel et al.

[11] Patent Number: 4,876,323

[45] Date of Patent: Oct. 24, 1989

[54] α-SUBSTITUTED ACRYLIC ACID ESTERS, THEIR POLYMERS AND METHOD OF SYNTHESIZING SAME

[75] Inventors: James F. Engel, Jackson County, Mo.; Thomas J. Byerley, Johnson County, Ks.; Howard W. Christie, Jackson County, Mo.

[73] Assignee: Midwest Research Institute, Kansas City, Mo.

[21] Appl. No.: 60,527

[22] Filed: Jun. 11, 1987

Related U.S. Application Data

[63] Continuation of Ser. No. 583,678, Feb. 27, 1984, Pat. No. 4,704,466.

[51] Int. Cl.$^4$ .................................... C08F 126/00
[52] U.S. Cl. ............................... 526/310; 526/312; 558/411; 560/205; 128/326; 156/307.3; 156/331.5
[58] Field of Search ............... 526/310, 312; 558/411; 128/1 R, 326; 156/307.3, 331.5

[56] References Cited

U.S. PATENT DOCUMENTS 4,130,576 12/1978 Hedaya et al. .................... 560/345
4,192,815 3/1980 Sheladyskov et al. ............ 556/420

OTHER PUBLICATIONS

Nitz, Theodore J. et al., *J. Org. Chem.*, vol. 46, (1981), pp. 2667–2671.

*Primary Examiner*—Paul J. Killos

*Attorney, Agent, or Firm*—Kokjer, Kircher, Bradley, Wharton, Bowman & Johnson

[57] ABSTRACT

α-Substituted acrylic acid esters, their polymers and adhesives therefrom, and methods of synthesizing these compounds. The compounds of the invention are useful as intermediates in the synthesis of isocyanato esters and can be polymerized to form an effective, non-toxic adhesive. The method of the invention encompasses utilizing the adhesive composition in biomedical applications, such as joining live animal tissue. Other adhesive applications are contemplated for living tissue and inanimate objects. The compounds are also used as monomers which can be polymerized, used in conjunction with other monomers as adhesive compositions, crosslinking agents, dye acceptor additives to vinylic polymers and useful chemical intermediates. The method of the invention encompasses synthesizing the aforementioned monomers and intermediates. Methyl α-(ethoxycarbonamido)acrylate is synthesized from either DL-serine or methyl pyruvate. For use as an intermediate, silyl substitution of the compound is accomplished by reacting the ester with trimethylchlorosilane. This α-substituted silated ester is used as an intermediate in the preparation of methyl α-isocyanatoacrylate, which can be polymerized with N-vinyl-2-pyrrolidone to produce a desirable adhesive. Analagous procedures, starting with L-ethyl serine and L-benzyl serine, respectively, are followed to arrive at the corresponding ethyl and benzyl esters.

11 Claims, No Drawings

α-SUBSTITUTED ACRYLIC ACID ESTERS, THEIR POLYMERS AND METHOD OF SYNTHESIZING SAME

This is a continuation of application Ser. No. 583,678, filed Feb. 27, 1984 U.S. Pat. No. 4,704,466.

This invention relates generally to compositions of matter and, more particularly, to α-substituted acrylic acid esters, their polymers and adhesives made therefrom, and to methods of synthesizing these compounds.

A number of α-substituted acrylate esters have been previously produced. See, for example, the compounds disclosed in U.S. Pat. No. 2,563,776 issued Aug. 7, 1951. Among the most useful and best known acrylate esters is methylmethacrylate which can be polymerized by free radical processes to a tough highly transparent material. It is also known that placement of a cyano group on the α-carbon will result in a highly reactive acrylate ester. Such compounds as methyl α-cyanoacrylate and other esters have found utility as fast setting adhesives for structural bonding applications.

The present invention encompasses a class of isocyanato esters and intermediates necessary to obtain same which can be utilized to produce new copolymers, adhesive compositions, cross-linking agents, dye acceptor additives to vinylic polymers and are useful intermediates. The adhesive compositions formulated according to the invention have particular utility as means of joining living tissue, both plant and animal. It is contemplated that the adhesives of the invention will find particular utility in conjunction with closing surgical incisions, repairing broken bones, skin grafting (including synthetic skin) and implacement of prosthesis devices. It was excepted that isocyanato esters would polymerize in a manner similar to the cyano esters previously identified, that is, through anionic mechanisms. This would result in useful homopolymers. Surprisingly, however, all attempts to initiate polymerization in this manner failed. Instead, it has been discovered that a useful copolymer can be produced through a free radical reaction by reacting the isocyanato esters with N-vinyl-2-pyrrolidone. The isocyanato group can be metabolized by living substances and will covalently bond to tissue to form an effective adhesive. It has also been unexpectedly discovered that the rate of copolymerization of the compounds of the invention can be effectively controlled by varying the quantity of catalyst employed.

A primary object of the present invention is to synthesize, isolate and positively identify a new class of compounds characterized by an isocyanato substitution on an acrylate ester.

Another important aim of the invention is to synthesize, isolate and positively identify certain α-substituted acrylic acid esters useful as intermediates in the synthesis of the isocyanato esters aforementioned.

An objective of the invention is to provide a new class of compounds as indicated in the objects preceding which can be polymerized to present useful polymers.

A corollary of the preceding objective is to provide a new class of compounds that can be polymerized to form an effective adhesive.

As another corollary to the objective preceding, one of the aims of our invention is to provide an effective, non-toxic adhesive for biomedical applications, including the joinder of hard and soft tissue and the implantation of synthetic objects into living tissue.

An objective of this invention is a method of joining living tissue, both plant and animal, utilizing an adhesive composition.

An important aim of our invention is to provide a new class of isocyanato substituted esters that are useful as monomers which can be polymerized, used in conjunction with other monomers as adhesive compositions, cross-linking agents, dye acceptor additives to vinylic polymers and useful chemical intermediates.

Other objects of the invention will be made clear or become apparent from the following description and claims.

The compounds of the invention have the following structure:

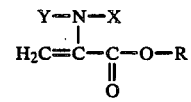

where X and Y are selected from one of the following pairs:

$$X = CO_2C_2H_5 \text{ and } Y = Si(CH_3)_3 \text{ and}$$

$$X = CO \text{ and } Y = \text{none}$$

and R may be $C_{20}$ or lower, linear or branched alkyls; aryl; alkaryl; aralkyl; halogenated alkyl ($C_{20}$ or lower); halogenated aryl; alkoxyalkyl; and alkoxyaryl. In the preferred embodiment of the invention R will be a $C_5$ or lower alkyl. In the general formula given when $X = CO_2C_2H_5$ and $Y = Si(CH)_3$, the compounds represented are the silated acrylate intermediates which are useful in synthesizing the compositions represented when $X = CO$ and $Y = $ none.

PREPARATION OF METHYL α-ISOCYANATOACRYLATE

The intermediate methyl α-(ethoxycarbonamido)acrylate has been successfully synthesized using two different starting materials. The preferred method is to form the methyl ester of DL-serine according to the following equation:

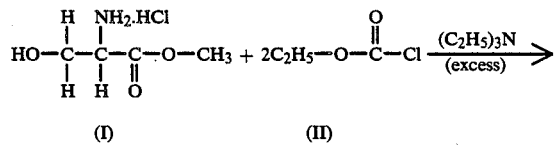

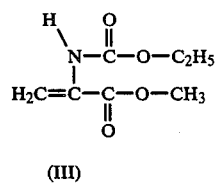

I = DL-methyl serine hydrochloride
II = ethyl chloroformate
III = methyl α-(ethoxycarbonamido)acrylate Alternatively, methyl α-(ethoxycarbonamido)acrylate may be prepared utilizing methyl pyruvate as a starting material. The reacton is as follows:

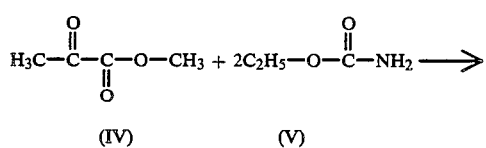

(IV)    (V)

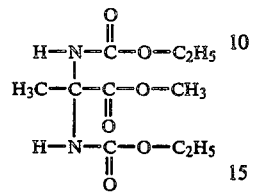

IV = methyl pyruvate
V = ethyl carbamate

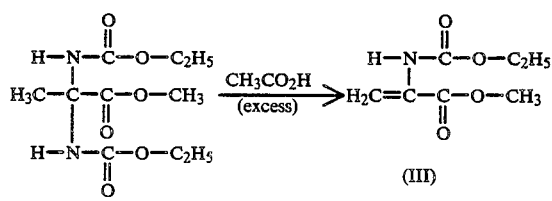

(III)

The methyl α-(ethoxycarbonamido)acrylate prepared according to one of the foregoing reactions is a useful intermediate for the synthesis of the monomer methyl α-isocyanatoacrylate, as discussed below.

The silyl substitution of methyl α-(ethoxycarbonamido)acrylate is accomplished by reacting the ester with trimethylchlorosilane according to the following equations:

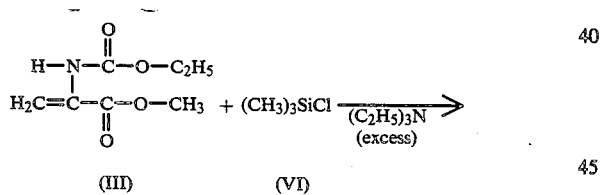

(III)    (VI)

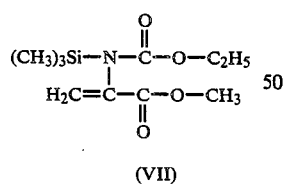

(VII)

VI = trimethyl chlorosilane
VII = methyl α-[N—(trimethylsilyl)-ethoxycarbonamido]acrylate The α-substituted silated ester is a second useful intermediate in the preparation of methyl α-isocyanatoacrylate as herein described. Care should be taken in preparation of both of the α-substituted ester intermediates to exclude all water.

The final step to obtain methyl α-isocyanatoacrylate is pyrolysis of the silated α-substituted ester at 150°–300° C. in the presence of argon or nitrogen, thus:

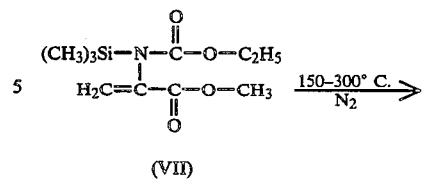

(VII)

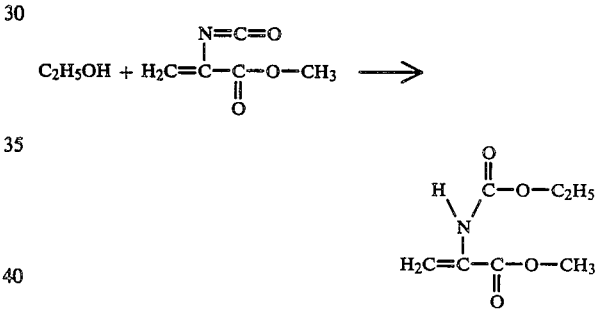

(VIII)    (IX)

VIII = methyl α-isocyanatoacrylate
IX = trimethylethoxysilane

The product of the pyrolysis may be purified to yield the desired methyl α-isocyanatocrylate by vacuum distillation in the presence of trinitrobenzene or through recrystallization from diethyl ether, or a combination of the foregoing. Confirmation of the existence of methyl α-isocyanatoacrylate has been obtained through use of IR and NMR spectra. Reaction of the product indicated to be methyl α-isocyanatoacrylate with ethanol results in an exothermic reaction and a viscous liquid product. The reaction proceeds as follows:

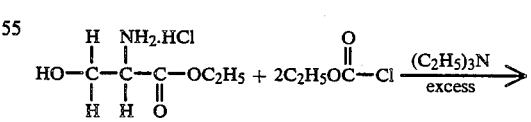

After evaporation of excess ethanol and trimethylethoxysilane, the IR spectrum is positive for the intermediate methyl α-(ethoxycarbonamido)acrylate. This is further unequivocal proof of the methyl α-isocyanatoacrylate product.

PREPARATION OF ETHYL α-ISOCYANATOACRYLATE

The intermediate ethyl α-(ethoxycarbonamido)acrylate has been successfully synthesized according to the following equation:

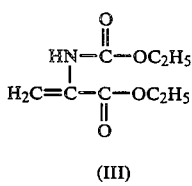

(I)    (II)

(III)

-continued

I = L-Ethyl serine hydrochloride
II = Ethyl chloroformate
III = Ethyl α-(ethoxycarbonamido)acrylate This material is a useful intermediate for the synthesis of the monomer ethyl α-isocyanatoacrylate, as discussed below.

The silyl substitution of ethyl α-(ethoxycarbonamido)acrylate is accomplished by reacting the ester with trimethylchlorosilane according to the following equation:

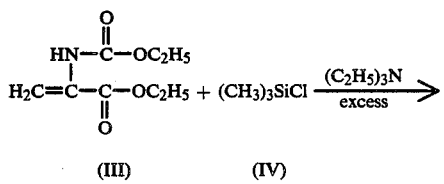

(III)   (IV)

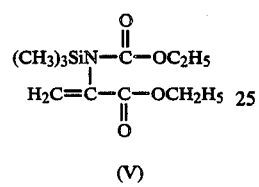

(V)

IV = Trimethylchlorosilane
V = Ethyl α-[N—(trimethylsilyl)ethoxycarbonamido]acrylate The α-substituted silyated ester is a second useful intermediate in the preparation of ethyl α-isocyanatoacrylate as herein described. Care should be taken in preparation of both of the α-substituted ester intermediates to exclude all water.

The final step to obtain ethyl α-isocyanatoacrylate is the pyrolysis of the silylated α-substituted ester at 250°–300° C. in the presence of an inert atmosphere such as nitrogen or argon, thus:

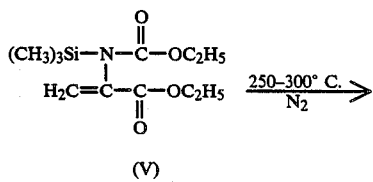

(V)

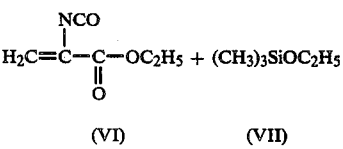

(VI)   (VII)

VI = Ethyl α-isocyanatoacrylate
VII = Trimethylethoxysilane

The product of the pyrolysis may be purified to yield the desired ethyl α-isocyanatoacrylate by vacuum distillation in the presence of trinitrobenzene or through recrystallization from diethyl ether, or a combination of the foregoing. Confirmation of the existence of ethyl α-isocyanatoacrylate has been obtained through the use of IR and NMR spectra. Reaction of the product indicated to be ethyl α-isocyanatoacrylate with ethanol results in an exothermic reaction and a viscous liquid product. The reaction proceeds as follows:

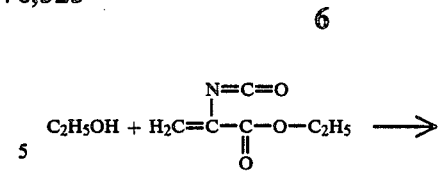

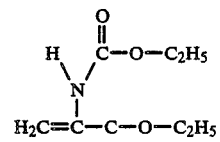

After evaporation of excess ethanol, the IR spectrum is positive for the intermediate ethyl α-(ethoxycarbonamido)acrylate. This is further unequivpocal proof of the ethyl α-isocyanatoacrylate product.

PREPARATION OF BENZYL α-ISOCYANATOACRYLATE

The intermediate benzyl α-(ethoxycarbonamido)acrylate has been successfully synthesized according to the following equation:

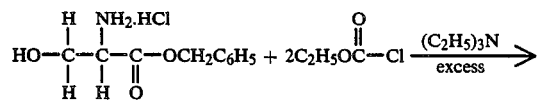

(I)   (II)

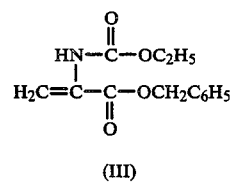

(III)

I = L-Benzyl serine hydrochloride
II = Ethyl chloroformate
III = Benzyl α-(ethoxycarbonamido)acrylate This material is a useful intermediate for the synthesis of the monomer benzyl α-isocyanatoacrylate, as discussed below.

The silyl substitution of benzyl α-(ethoxycarbonamido)acrylate is accomplished by reacting the ester with trimethylchlorosilane according to the following equation:

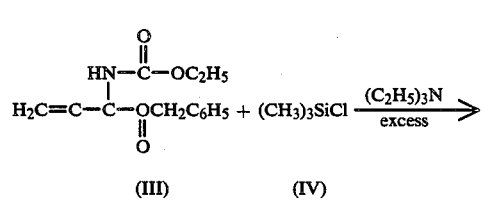

(III)   (IV)

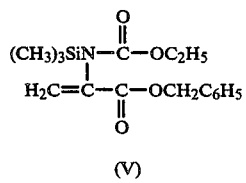

(V)

IV = Trimethylchlorosilane
V = Benzyl α-[N—(trimethylsilyl)ethoxycarbonamido]acrylate The α-substituted silylated ester is a second useful intermediate in the preparation of benzyl α-isocyanatoacrylate as herein described. Care should be taken in preparation of both of the α-substituted ester intermediates to exclude all water.

The final step to obtain benzyl α-isocyanatoacrylate is the pyrolysis of the silylated α-substituted ester at 150°–300° C. in the presence of an inert atmosphere such as nitrogen or argon, thus:

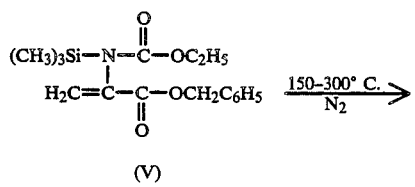

(V)

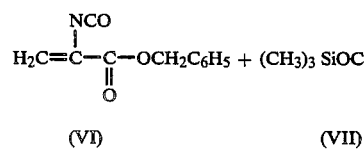

(VI)           (VII)

VI = Benzyl α-isocyanatoacrylate
VII = Trimethylethoxysilane

The product of the pyrolysis may be purified to yield the desired benzyl α-isocyanatoacrylate by vacuum distillation in the presence of trinitrobenzene or through recrystallization from diethyl ether, or a combination of the foregoing. Confirmation of the existence of benzyl α-isocyanatoacrylate has been obtained through the use of IR and NMR spectra.

It has been found that the compositions of the invention can be copolymerized to form useful adhesives. For example, methyl α-isocyanatoacrylate can be polymerized with N-vinyl-2-pyrrolidone, preferably in a ratio of about 60:40. The reaction is accelerated using a free radical catalyst such as hydrogen peroxide, benzoyl peroxide or α,α'-azodiisobutyronitrile. The reaction is exothermic and proceeds at room temperature or above. Addition of up to 2% (by weight) $H_2O_2$ (50% by weight aqueous solution) to the monomer mixture provides an effective catalyst for the polymerization reaction. More or less catalyst can be utilized to provide a broad range of control over the reaction time although above 2% concentrations the gel time becomes very rapid, limiting the usages of the monomer mixture. As previously indicated, the ability to control the reaction time of the polymerization reaction is a significant factor in adopting the adhesive of the invention to a braod range of biomedical applications. A gel time of 30–60 seconds is generally preferred where the monomer mixture is to be used as an adhesive and such can be easily obtained utilizing about 1% (by weight) $H_2O_2$ in a 50% (by weight) aqueous solution.

The following examples are indicative of the procedure to be followed in obtaining the compositions of the invention according to the aforedescribed general method.

EXAMPLE 1

Methyl α-isocyanatoacrylate

To 1 mole, 159.4 g, of DL-methyl serine hydrochloride and 5 moles, 493 ml, of ethyl chloroformate in 1 liter of chloroform is added 7.5 moles, 1080 ml, of triethylamine (TEA). Alternatively, the ethyl chloroformate may be added after the other two components have been combined. The TEA is added gradually to control the reaction temperatures at reflux. After addition of TEA additional heat is applied and refluxing is continued for approximately 12 hours. Hydroquinone (4 g) is added to the product mixture as a polymerization inhibitor.

Excess chloroform is evaporated and the remaining product diluted with benzene and filtered. The triethylamine hydrochloride is slurried, washed twice with benzene, filtered and concentrated. The concentrate is again filtered and the triethylamine hydrochloride salt washed with additional benzene. A second concentration of the benzene wash and filtrate is carried out. An additional 2 g of hydroquinone inhibitor is added and the product is vacuum distilled at 79°–147° C. (pot temperature) and pressure of 0.17 to 1.4 torr. A fraction taken at 65°–72° C., 0.17 to 1.4 torr is redistilled in the presence of hydroquinone. A fraction is collected at 45°–47° C., 0.5 torr. Analysis by both IR and NMR spectroscopy confirm the product to be methyl α-(ethoxycarbonamido)acrylate. The elemental analysis for $C_7H_{11}NO_4$ is: theoretical, C, 48.55; H, 6.40; N, 8.09; Found: C, 48.69; H, 6.60; N. 8.31.

The methyl α-(ethoxycarbonamido)acrylate is subjected to silyation as follows: To 34.6 g, 0.2 mole, of the acrylate product is added 60 g, 0.6 mole, of triethylamine. Trinitrobenzene is added as a polymerization inhibitor. The reaction mass is heated to reflux, under nitrogen, and stirred. Forty-three grams, 0.4 mole, trimethylchlorosilane is added dropwise, the mixture heated to 75°–78° C., and allowed to reflux for about 12 hours. The reaction product is concentrated on a rotary evaporator, diluted with ether and filtered. The triethylamine hydrochloride salt is washed with additional ether, filtered and the ether removed on a rotary evaporator. The resulting product is vacuum distilled at 63°–65° C. (pot temperature), 0.2–0.3 torr. The distillation product is then redistilled at 57° C., 0.05 torr. The infrared and NMR spectra for this product confirm that it is methyl α-[N-trimethylsilyl(ethoxycarbonamide)]acrylate.

Pyrolysis of the silyl derivative occurs at 150°–300° C., preferably carried out at about 275° C. to yield the products methyl α-isocyanatoacrylate and trimethylethoxysilane. Both vapor phase and liquid phase pyrolysis can be utilized. In a preferred technique, the crude pyrolysate is transferred to a still pot on a high vacuum rack, frozen with liquid nitrogen and degassed under a vacuum of $10^{-6}$ torr. The product is then allowed to come to room temperature while molecular distillation into two traps is performed.

The first trap is a dry ice mixture at −50° C. and the second is chilled with liquid nitrogen. Distillation is continued until no further volatiles are being removed from the pot. The product in the −50° C. trap is substantially pure methyl α-isocyanatoacrylate. NMR and infrared spectra confirm the structure of the product.

Methyl α-isocyanatoacrylate is polymerized with N-vinyl-2-pyrrolidone in the manner previously described. When used as a biomedical adhesive, the two monomers and catalyst mixture may be applied dropwise to a fresh, sponged incision. The incision is clamped or otherwise held for a period of thirty seconds (in some cases one to two minutes) to allow the adhesive to bond the two tissues together.

EXAMPLE 1

Alternate Embodiment

As discussed previously, an alternative route to synthesizing methyl α-(ethoxycarbonamido)acrylate is to utilize methyl pyruvate as a starting material. To 0.5 mole (B 51 g) of methyl pyruvate is added 1.0 mole, 89 g, of ethyl carbamate and 200 ml of toluene. The mixture is heated under reflux for about 12 hours. About 3 drops of p-toluene sulfonic acid is added and the mixture is then heated under reflux for another 2 hours. After cooling to room temperature, the toluene solution is washed with water containing a small amount of $NaHCO_3$, to neutralize the p-toluene sulfonic acid. The aqueous and toluene phases are then separated and the toluene removed on a rotary flask evaporator. To the remaining residue from the toluene phase is added 0.2 g of hydroquinone and 200 ml of acetic acid. The mixture is heated to reflux for 15 minutes and the acetic acid is then removed by vacuum distillation at 20 torr pressure. An additional 0.1 g of hydroquinone is added to the pot and the pressure is decreased to 2 torr and distillation continued. Fractions are taken within the range of 50°–98° C. (pot temperature), 2.0–2.5 torr and then redistilled. A fraction is taken at 90° C., 2.1 torr. This is α-methyl α-(ethoxycarbonamido)acrylate. The remainder of the procedure to obtaining the silated intermediate and the monomer methyl-α-isocyanatoacrylate is as described in the previous example.

EXAMPLE 2

Ethyl α-isocyanatoacrylate

To 10 g (0.059 mole) of L-ethyl serine hydrochloride, 70 ml (excess) of triethylamine, and 65 ml of chloroform in an ice bath was added dropwise 32.0 g (0.295 mole) of ethyl chloroformate. When the addition was completed, the mixture was refluxed for 4 hr. The reaction mixture was filtered and the filtrate was stripped of solvents. The residue was dissolved in benzene and washed with water. The solvent was evaporated, a small amount of hydroquinone was added to the residue, and vacuum distillation gave 9.7 g (88%) boiling at 84° C., 0.35 torr. Analyses by both IR and NMR spectroscopy confirm the product to be ethyl α-(ethoxycarbonamido)acrylate.

The ethyl α-(ethoxycarbonamido)acrylate is subjected to silylation as follows: To 9.7 g (0.52 mole) of the acrylate product in 15.7 g (0.156 mole) of triethylamine and 25 ml of benzene was added 10.8 g (0.104 mole) of trimethylchlorosilane dropwise. The mixture was refluxed for 16 hr, then filtered, and the filtrate was stripped of solvents. The residue was dissolved in benzene, washed with water, and stripped of solvent. After the addition of hydroquinone, vacuum distillation gave product boiling at 70° C., 0.20 torr. The IR and NMR spectra for this product confirm that it is ethyl α-[N-trimethylsilyl(ethoxycarbonamido)]acrylate.

Pyrolysis of the silyl derivative occurs at 250°–300° C., preferably carried out at about 275° C. to yield the products ethyl α-isocyanatoacrylate and trimethylethoxysilane. Purification of the crude pyrolysate is accomplished by a molecular distillation at room temperature at 0.15 torr into a two-trap system. The first trap, in ice water at 0° C., retains the pure ethyl α-isocyanatoacrylate, and the second trap at dry ice temperature retains the trimethylethoxysilane. NMR and IR spectra confirm the structure of the product.

EXAMPLE 3

Benzyl α-isocyanatoacrylate

To 10 g (0.043 mole) of L-benzyl serine hydrochloride, 70 ml (excess) of triethylamine, and 65 ml of chloroform in an ice bath was added dropwise 23.4 g (0.216 mole) of ethyl chloroformate. When the addition was completed, the mixture was refluxed for 6 hr. The reaction mixture was filtered and the filtrate was stripped of solvents. The residue was dissolved in benzene and washed with water. The solvent was evaporated, a small amount of hydroquinone was added to the residue, and vacuum distillation gave 4.0 g boiling at 125° C., 1.0 torr. IR and NMR spectra confirm the product to be benzyl α-(ethoxycarbonamido)acrylate.

The benzyl α-(ethoxycarbonamido)acrylate is subjected to silylation as follows: To 2.5 g (0.10 mole) of the acrylate product in 2.0 g (0.02 mole) of triethylamine and 20 ml of benzene was added 1.1 g (0.01 mole) of trimethylchlorosilane dropwise. The mixture was refluxed for 2 hr, then filtered, and the filtrate was stripped of solvents. The residue was dissolved in benzene, washed with water, and stripped of solvent. After the addition of hydroquinone, vacuum distillation gave product boiling at 126° C., 0.20 torr. The IR and NMR spectra for this product showed that pyrolysis had occurred during the distillation and that the predominate material collected was benzyl α-isocyanatoacrylate.

Toxicological studies done on animals implanted with methyl α-isocyanatoacrylate/N-vinyl-2-pyrrolidone copolymer, as well as the pure monomer methyl α-isocyanatoacrylate, indicate no significant tissue reaction to this composition. It is known that poly(vinyl pyrrolidone) in aqueous solution is useful as a blood plasma extender without adverse consequences to the human body, and the results obtained with regard to the copolymer are consistent therewith.

We claim:

1. A composition comprising: the product of copolymerization of N-vinyl-2-pyrrolidone and R-α-isocyanatoacrylate where R is selected from the group consisting of $C_1$ to $C_5$ alkyls and benzyl.

2. A composition as set forth in claim 1, wherein said copolymerization occurs in the presence of a free radical catalyst.

3. A composition as set forth in claim 2, wherein said free radical catalyst is selected from the group consisting of hydrogen peroxide, benzoyl peroxide and α,α'-azodiisobutyronitrile.

4. A composition comprising: the product of copolymerization of methyl α-isocyanatoacrylate and N-vinyl-2-pyrrolidone.

5. A composition as set forth in claim 4, wherein said copolymerization occurs in the presence of $H_2O_2$.

6. A method of joining together two components comprising: applying to at least one of the components a layer of a composition comprising a mixture of (a) a first monomer selected from the group consisting of R-α-isocyanatoacrylate where R is selected from $C_1$ to $C_5$ alkyls and benzyl and (b) the monomer N-vinyl-2-pyrrolidone; bringing the two components into contact; and holding the two components in contact until they are adhered.

7. A method as set forth in claim 6, wherein said mixtures comprises an effective quantity of a free radical catalyst for accomplishing polymerization in a period of about 30 to 60 seconds.

8. A method as set forth in claim 7 wherein said mixture comprises up to 2% by weight of a 50% by weight aqueous solution of $H_2O_2$.

9. A method of joining together two living tissues comprising: applying to at least one of the tissues a layer of a composition comprising a mixture of a first monomer selected from the group consisting of methyl, ethyl and benzyl α-isocyanatoacrylate and N-vinyl-2-pyrrolidone in the presence of an effective quantity of a free radical catalyst to provide a gel time for the composition of from 30–60 seconds; bringing the two tissues into contact; and holding the two tissues in contact until they are adhered.

10. A method as set forth in claim 9, wherein said catalyst is $H_2O_2$ in a quantity of about 1% to 1½% by weight of a 50% by weight aqueous solution.

11. A method of joining together two living tissues comprising: applying to at least one of the tissues a layer of a composition comprising a mixture of the monomers methyl α-isocyanatoacrylate and N-vinyl-2-pyrrolidone in the presence of an effective quantity of $H_2O_2$ to provide a gel time for the composition of from 30–60 seconds; bringing the two tissues into contact; and holding the two tissues in contact until they are adhered.

* * * * *